United States Patent [19]

Wiegel

[11] Patent Number: 4,679,254
[45] Date of Patent: Jul. 14, 1987

[54] PROTECTIVE SHIELD FOR A WELDERS MASK

[76] Inventor: Hendrikus P. Wiegel, Karel Doormanstraat 6, 2631 AM Nootdorp, Netherlands

[21] Appl. No.: 819,680

[22] Filed: Jan. 17, 1986

[30] Foreign Application Priority Data

Jan. 18, 1985 [NL] Netherlands ......................... 8500129
Nov. 29, 1985 [NL] Netherlands ......................... 8503315

[51] Int. Cl.$^4$ ............................................. A61F 9/06
[52] U.S. Cl. .................................... 2/8; 200/61.58 R; 200/DIG. 2
[58] Field of Search ........... 2/8; 200/61.58 R, DIG. 2

[56] References Cited

U.S. PATENT DOCUMENTS

| | | | | |
|---|---|---|---|---|
| 3,484,156 | 12/1969 | Militello | ................................ | 351/44 |
| 3,540,058 | 11/1970 | Lo Guidice | ................................ | 2/8 |
| 3,833,936 | 9/1974 | Lo Guidice | ................................ | 2/8 |
| 3,838,247 | 9/1974 | Finger et al. | ................................ | 2/8 X |
| 4,510,625 | 4/1985 | Mizuki | ................................ | 2/8 |
| 4,546,498 | 10/1985 | Fantin | ................................ | 2/8 |

FOREIGN PATENT DOCUMENTS 0455648 2/1928 Fed. Rep. of Germany .
0172118 11/1975 Netherlands .
0224784 4/1943 Switzerland .
704714 2/1954 United Kingdom .
0878847 10/1961 United Kingdom .

OTHER PUBLICATIONS

Netherlands Search Report for Application 85-00129.

Primary Examiner—Louis K. Rimrodt
Attorney, Agent, or Firm—Wegner & Bretschneider

[57] ABSTRACT

A protection shield, e.g., a welders mask, has an only slightly transparent screen such as a welder's glass movable in front of and away from an opening in the shield by a reversible electric motor, driving the screen directly. The screen is guided by rods in the shield, which it engages in only a few discrete points. Motor, screen and guides are easily removable from and insertable into the shield. This gives a simple and reliable structure with low energy requirement. There are provisions for charging a battery energizing the motor either by solar cells or by an external source. A hand operated switch is provided with means to be carried on a finger of the user, which switch operates the screen. A spatter glass is taken up in the shield in guides so as to be easily removable and replaceable and so that its thickness is not critical.

16 Claims, 4 Drawing Figures

PROTECTIVE SHIELD FOR A WELDERS MASK

This invention relates to a protective shield to protect the eyes against vivid light, such as a welders mask, helmet or window, with an only slightly transparent screen such as a welding glass, with means for moving this screen by an electric motor to make it slide in its own plane between a position in a light transparent opening in the body of the shield and a position to free said opening for light transmission therethrough and to a hand switch particularly adapted for use therewith.

Such a shield is known, e.g. from U.S. Pat. No. 3,833,936. Therein, there is an electric motor mounted in the body of the shield with its axis parallel to the direction of movement of the screen. A gear train with bevelled and other gear wheels connects the drive spindle of this motor to two pinions one at each side of the screen and each one in engagement with a toothed rack on the screen at the same side thereof.

This mechanism is rather complicated and comprises a considerable number of rather expensive parts, there have to be two racks and the mechanism is vulnerable as to contamination, in particular between the several gear wheels, which would cause stiff running. There is much friction between the screen and its guides. All this means that relatively high energy requirements have to be met.

Jamming is nevertheless avoided by the considerable speed reduction ratio between the motor spindle and the screen, but this means more time needed to move the screen, which is undesirable in many applications such as in welders masks.

This invention aims at improving such protective shields with respect to the considerations given above and to this end such a shield is, according to the invention, characterized in that the electric motor has a toothed or friction pinion in direct contact with a toothed or friction rack on the screen, the guide means in the shield along at least one of said edges being taken up in the shield in a manner so as to be easily detachable therefrom.

It is thus possible to guide the screen in a very limited number of points, three points being enough, and thereby and by the direct drive of the screen on one side the total friction of the moving screen is very low and its guiding is nevertheless excellent. The structure is simple, has a very low number of parts and is thus less vulnerable and less expensive to pollutions and contaminations. Only very little energy is required to move the screen and the time necessary for moving the screen is very short.

The invention also relates to details of the guide and drive means as will be explained below.

In a preferred embodiment of the protective shield according to the invention the electric motor is also easily removable and insertable by being taken up by a carrier, which is slidable frictionally in guides in the body of the shield so as to be easily removable from and insertable into the shield.

In said U.S. Pat. No. 3,833,936 there is a trip switch on the shield, operated by the welder through a mouthpiece and a tube filled with fluid. Moreover there are limit switches having contacts in the shield body near the four corners of the moving screen, which screen itself carries contacts to cooperate therewith, said limit switches and said human operated switch being taken up in a double-throw circuit.

The present invention also aims at improving and simplifying the electric circuit and the parts thereof including the switches. Thereto, a protective shield according to the invention is preferably characterized in that the screen has a protruding part close to each end thereof as seen in its sliding direction, there being a switch in the shield body cooperating with said protruding parts so that, when the screen reaches one end position, one of the protruding parts contacts said switch to move it into one position and when said screen reaches the other end position the other protruding part moves the switch into the other position, said switch being taken up in an electric circuit to energize the electric motor to move the screen, there being a two-way switch operable by the user, taken up with said switch in the shield body, also being a two-way switch, in a double throw circuit in the opposite energizing leads for the reversible electric motor, so that the motor is de-energized in each terminal position of one of the switches in one of the terminal positions of the other switch which, when put in its other terminal position, energizes the motor in the direction of movement of the screen to the other terminal position. This not only simplifies the electric circuit but also makes it more reliable.

For the switch operable by the user a hand operated electric switch is according to the invention preferred over other types of switches, such as foot or mouth operated switches giving difficulties as to hindrance, space available inside or outside the shield, hygiene and risk of wrong operation by disturbing factors. But also hand operated switches give problems. The user e.g. the welder, also has to use his hands for other purposes, such as for welding itself, for keeping his own body in the desired position, for positioning workpieces, for operating a light hammer to remove scales from the weld etc. The concerning switch may be carried by the shield, e.g. the welder's mask, or by an electrode holder or other part which the user has to handle. None of such possibilities is favourable, either because operation is only possible when the user interrupts holding or operating other parts or because he cannot move away from his work, from a certain tool or workpiece, without having to disconnect the electric connection between the switch and the protective shield in cases where he carries the shield himself, such as a welder's mask.

This invention also aims at bringing improvement in these respects and in view thereof it is according to the invention preferred to use a hand operated switch having a switch body and a brace, with a space between them adapted to take up a human finger between the switch body and the brace for carrying the switch by said finger.

It is thus possible for the user to perform other operations by hand, to handle an electrode holder etc. and simultaneously be free to actuate the switch at any desired moment. Such a switch may have a switch body which is so flat, narrow and thin that a working glove may be worn over it without discomfort. The brace may even form an inherent part of a glove.

The brace may be rigid or flexible. In both cases it is preferred to choose sizes and shapes for brace and switch body so that the space between brace and switch body is so narrow and/or of such a shape that the switch has two comfortable equilibrium positions, one in which the feeling side of the finger rests on the switch body and the other one having the switch body on the back side of the finger, the switch being turnable on the finger between these position. With the switch at the back of the finger it is possible for the user e.g. to use a hammer or other tool requiring the exertion of forces thereon by hand without operating the switch.

The invention will now be described in more detail with reference to the enclosed drawings giving a preferred embodiment of a protective shield, a switch and an electric circuit of the system with such a shield. In said drawings.

Figure 1:
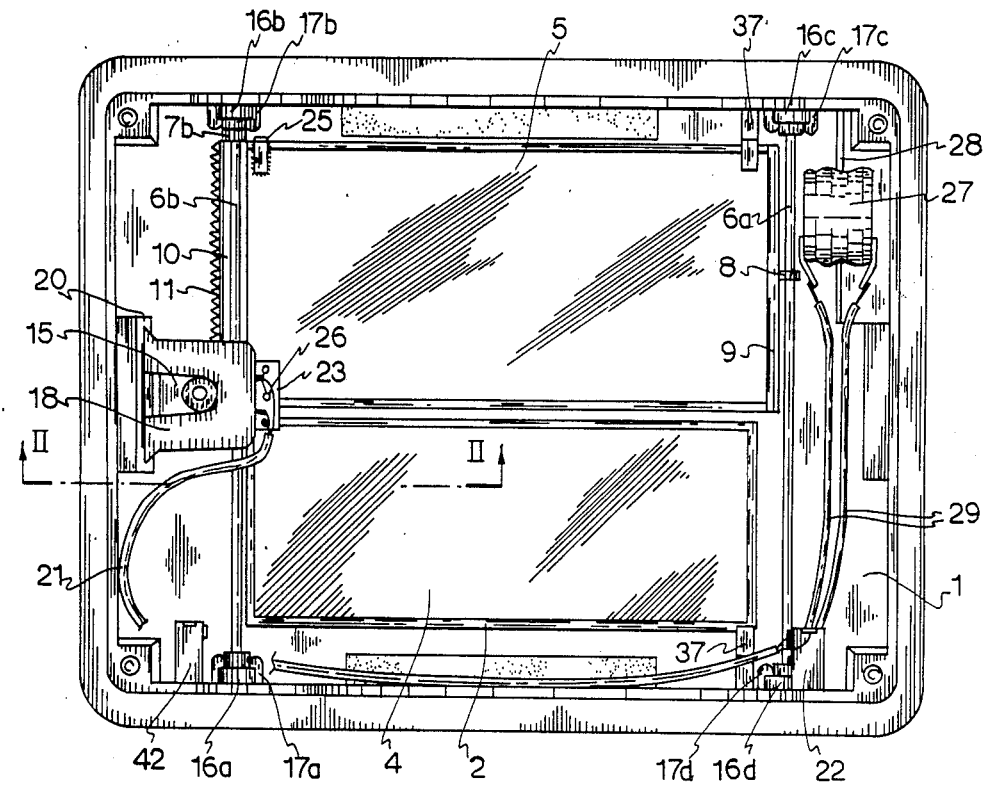
FIG. 1 is a back view (elevation) of the central part of a welder's mask according to the invention.

A welder's mask of usual shape has means to be carried by the welder in a usual way, such as by hand or, as is more usual nowadays, by the head of the welder. It has a substantially rectangular central opening, along the edges of which a central casing 1 is mounted, e.g. by screws not shown near the four corners of casing 1 engaging screw-threaded holes therein, shown in FIG. 1.

Casing 1 has a rectangular opening with edge 2. The opening is closed by a transparent spatter glass 4 enclosed between L-shaped guides 3 at the outside of casing 1. Resilient strips 13 urge the glass 4 resiliently forwardly into contact with the front edges of the guides 3. At the left in FIG. 2 the guide edges 3 are interrupted so that the glass 4 may easily be moved slidingly out of the mask in order to be cleaned or replaced by another glass. The resilient strips 13 and the space within the L-shaped guides 3 allow spatter glass (or plastics) plates 4 of different thicknesses to be used. Above the opening with edge 2 the closed face of the casing 1 may carry a series of solar cells not shown in FIGS. 1 and 2 but indicated as 40 in FIG. 4, for charging a chargeable battery 27 to be described, and these solar cells may be protected by the same spatter glass 4, then having a much larger surface (height in FIG. 1), or by a separate spatter glass, which may be guided by similar guides as the guides 3 in the same way as glass 4, also being urged forwardly by resilient strips 13 in said guides and removable and replaceable by sliding through the open end of the guides 3 as described for glass 4.

At the inside of casing 1 there is an only slightly transparent screen 5 such as a welder's glass, movable up and down (in FIG. 1) from a position to leave the opening 2 entirely free (as in FIG. 1) to a position to cover this opening entirely and thus protect the eyes of the welder during welding.

This screen 5 is connected to guide rods 6a and 6b. Thereto the right hand edge of this screen (in FIG. 1) carries a fork 8 engaging with its tongs one to each side of rod 6a, said fork being part of a strip 9 connected to screen 5.

At the left in FIG. 1 the screen 5 is rigidly connected to a strip 10 having at each end a lug 7a, 7b, engaging with its eye around rod 6b. The screen 5 is thus guided correctly by the rods 6a and 6b in its movement between the two positions described but only in three points. At each end each rod 6a, 6b has a supporting bracket 16a, 16b, 16c, 16d, frictionally taken up between two opposite take-up parts 17a, 17b, 17c, 17d, rigidly united with casing 1. The brackets 16a to d may be snapped into the space between each two take-up parts 17a to d and be removed therefrom under friction by movements perpendicularly to the plane of FIG. 1.

A reversible electric motor 15 is taken up between the top leg 18 and the bottom leg 19 of a carrier taken up frictionally for up and down movement (as seen in FIG. 1) between the swallow-tail guides of a carrier part 20 in casing 1. Leg 19 also carries a two-way slide switch 23. The slidable operating part 24 thereof is operated by protrusions 25, one at each end (upper and lower end as seen in FIG. 1) of the screen 5. These protrusions are preferably somewhat elastic or covered with elastic material to operate switch 23 more flexibly. Electric leads 26 connect this switch to the electric system and the electric motor is connected by electric leads 21 to this system in a manner to be described below.

The spindle 14 of the electric motor 15 carries a pinion 12, which is in driving engagement with a toothed rack 11 integral with strip 10 on screen 5.

By the structure described it is easily possible to assemble the structure by inserting rod 6b through the eyes of the lugs 7a, 7b of screen 5, then to mount brackets 16a, 16b on this rod and to mount brackets 16c, 16d on rod 6a. While fork 8 is made to engage rod 6a, the rods 6a and 6b with screen 5 are now inserted in casing 1 by pushing the brackets 16a–d into the take-up parts 17a–d. It is easy to apply rod 6b first, then bring rod 6a between the tongs of fork 8 and then to apply rod 6a while tilting screen 5 around rod 6b. The electric motor is now mounted by pushing it with its carrier 18, 19 into the guides on carrier part 20 in casing 1 until pinion 12 engages rack 11. It is also very easy to disassemble the parts e.g. for cleaning, by the opposite sliding movements for removing the electric motor and the screen with the rods 6a, 6b.

A chargeable battery 27 is taken up slidingly between guides 28 in casing 1 and is taken up in the electric circuit by electric leads 29. Battery 27 can be moved by sliding between those guides so as to be removed, cleaned and replaced easily.

A plug-connector 22 in the bottom of casing 1 serves for making an electrical connection with a hand switch to be described and may also be used for making an electrical connection with an electric source for charging battery 27 if there are no solar cells or if these do not supply enough charging energy. For such charging it is also possible to use a separate plug connector 42 shown at the left in FIG. 1.

At the right in FIG. 1 there are two resilient arresting strips 37. The screen 5 has top and bottom edges, which are thickened so as to protrude somewhat in the direction of the eye when looking at FIG. 1. When the screen is in the top or bottom position, one of these strips engages over one of these thickened edges to arrest the screen, which is particularly useful to prevent the screen from falling down when in the top position. The electric motor 15 may be so as to help in keeping the screen in position by magnetical positioning of its rotor, but as a very light electric motor is sufficient, it is better not to rely thereon fully for such arresting.

Figure 2:
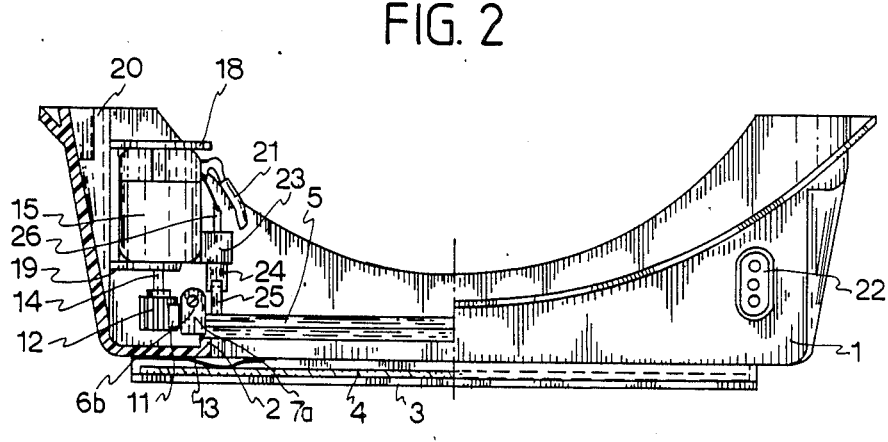
FIG. 2 shows a view of the bottom of said central mask part from below at the right and a section along the line II—II in FIG. 1 at the left.
Figure 3:
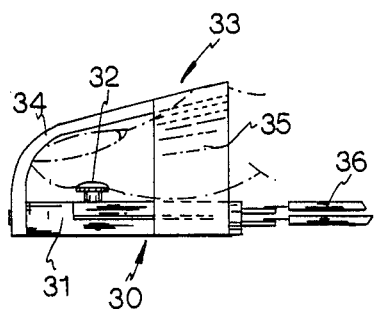
FIG. 3 shows a side view of a hand switch for use together therewith.

FIG. 3 shows a hand-operated two-way switch 30 according to the invention, for use with the shield of FIGS. 1 and 2. The switch body 31 has a push button 32, resiliently urged to its top position corresponding to one of its switching positions, the other switching position being taken up when the button 32 is depressed. A brace 33 is mounted around the switch body 31 or connected thereto in another way and consists of a longitudinal part 34 and a peripheral part 35. It may also consist of a fully closed cap with only one opening to introduce the operator's finger therethrough. A three-lead electric cable 36 connects this switch through connector 22 to the electric system in casing 1. The brace 33 may be of metal or plastics material or of textile material, either flexible or substantially rigid. A finger, e.g. a thumb, of the welder fits between the parts 31, 33 and 34 as shown so as to rest on button 32. If the brace 33 is substantially rigid, it is preferably of oval shape, wider than high, so that the brace fits the finger but can be turned round thereon to have switch casing 31 and button 32 rest either at the back (top) side of the finger or at the touch side thereof. Also when the brace 33 is flexible, those two positions may be stable in view of the rather flat form of switch body 31 as the human fingers perpendicularly to the nail are thinner than in the width direction.

Now, turning to FIG. 4, the operation of this switch and of the protective shield will be described in more detail.

In the position shown the motor 15 is energized because a circuit is closed through switch 31 and the sliding switch 23 in the casing 1 and through battery 27. Motor 15 will thus rotate, so that pinion 12 will move screen 5 in one of the directions indicated by double arrow 43. The protrusions 25 on the screen are positioned so that operating part 24 is positioned in the path thereof. By the movement of screen 5, one of the protrusions 25, e.g. the bottom one in FIG. 4, will contact part 24 and will move it from the full line position of the switch in FIG. 4 to the dotted line position. Thereby the electric current to motor 15 is interrupted and thus it stops.

Figure 4:
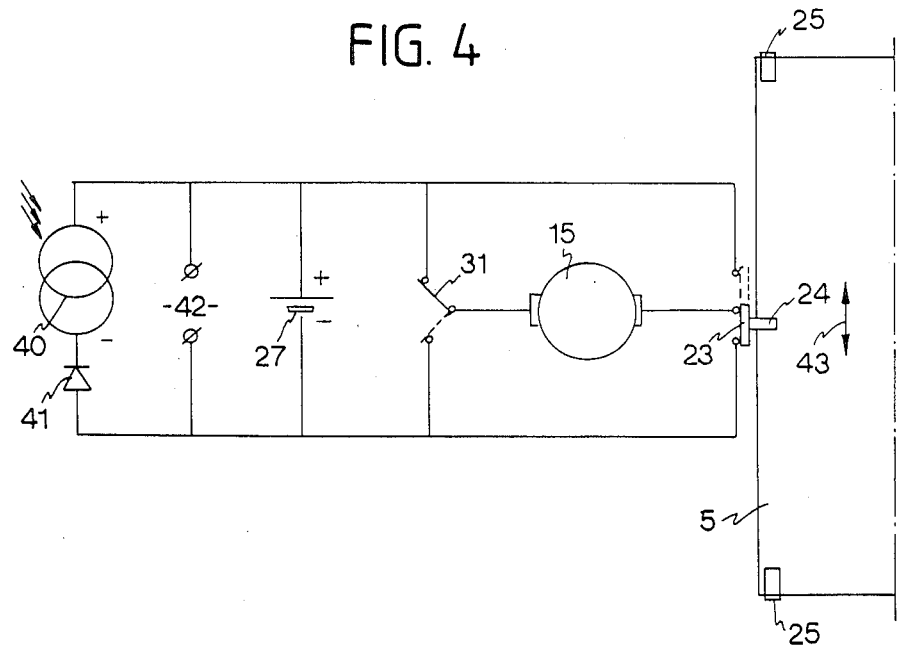
FIG. 4 shows somewhat simplified electric circuit for the device of the preceding Figures.

Now, if switch 31 is operated, both switches 23 en 31 will be in the dotted-line position of FIG. 4, so that the circuit through motor 15 is again closed, but in the opposite direction to rotate motor 15 in the opposite direction. Screen 5 will thus move in the opposite direction until the top protrusion 25 will operate part 24 of switch 23 to bring it back to the full-line position.

This means that by one movement of button 32 of switch 31, either depressing or allowing it to move upwardly resiliently, motor 15 is energized during a very short period to move the screen 5 to the opposite position, after which the motor is made dead. It is a matter of choice whether the screen 5 is in position before window 2 when button 32 is depressed or when button 32 is free to take up its top position.

Battery 27 is connected through a diode 41 to the set of solar cells 40 generating a charging current for charging it. Diode 41 prevents flow from the battery in the wrong direction through the solar cells 40.

The charging device for the battery is preferably of the type with built-in current limiter.

Within the frame of the invention many variations are possible. So, the rack 11 and pinion 12 may be replaced by a friction strip and cooperating friction wheel. The fork 8 on screen 5 may be replaced by a lug like lugs 7a, 7b.

I claim:
1. A shield for protecting eyes, comprising:
 a body having an opening;
 an eye-protecting screen, slidable between first and second positions in which the screen covers and uncovers the opening;
 a plurality of guide means in the shield for guiding the screen between the first and second positions, extending substantially parallel to the direction of screen movement;
 a reversible electric motor secured to the body, comprising a drive shaft and a toothed or friction pinion secured to the drive shaft, for moving said screen between the firsr and second positions, said screen comprising a toothed or friction rack in direct contact with the pinion; and
 means for activating the motor to move the screen between the first and second positions.

2. A shield according to claim 1, wherein the drive shaft is substantially perpendicular to the main plane of the screen.

3. A shield according to claim 2, further comprising a transparent spatter plate covering the opening in the body and a second guide means on the body for slidably accepting the spatter plate, comprising a resilient strip for urging the spatter plate into engagement with the second guide means and allowing the second guide means to accept spatter plates of varying thickness.

4. A shield according to claim 1, further comprising mounting guides on said body for accepting said motor, to allow the motor to be easily inserted into and removed from the shield.

5. A shield for protecting eyes, comprising:
 a body having an opening;
 an eye-protecting screen, slidable between first and second positions in which the screen covers and uncovers the opening;
 guide means in the shield for guiding the screen between the first and second positions, comprising:
  a plurality of rods secured to the body, extending substantially parallel to the direction of screen movement; and
  a plurality of discrete protruding parts secured to the screen for slidably engaging said rods, said protruding parts having a dimension in the direction of screen movement which is substantially smaller than the dimension of the screen in the direction of screen movement;
 a reversible electric motor secured to the body, comprising a drive shaft and a toothed or friction pinion secured to the drive shaft, for moving said screen between the first and second positions, said screen comprising a toothed or friction rack driven by the pinion; and
 means for activating the motor to move the screen between the first and second positions.

6. A shield according to claim 2, wherein one of said rods is easily detached from said body and the protruding parts engaging the easily detached rod comprise lugs having an opening which slidably engages the rod.

7. A shield according to claim 2, wherein at least one of the protruding parts comprises a fork having an open end which engages one of said rods.

8. A shield according to claim 7, wherein at least one of the protruding parts comprises a fork having an open end which engages one of said rods.

9. A shield according to claim 2, wherein the number of protruding parts is three, with two of the protruding parts being located on one edge of the screen and one on an opposite edge of the screen.

10. A shield according to claim 2, further comprising supporting brackets at the ends of the rods and means on the body for frictionally engaging the brackets, said brackets being slidable in and out of the means for engaging in a direction substantially perpendicular to the main plane of the screen.

11. A shield according to claim 2, wherein the screen further comprises two protrusions, disposed at positions on the screen which are in the vicinity of opposed end positions with respect to the direction of screen movement, and the body comprises a first two-way switch movable by one of said protrusions to a first position and to a second position by the other protrusion, the means for activating the motor comprising:

said first two-way switch;

a second two-way swtch operable by a user of the shield, said first and second switches being connected with opposite energizing leads for the motor in a double-throw circuit comprising a power source, each position of the first two-way switch having a corresponding position in the second two-way switch in which the motor is deactivated, the motor being activated to drive the screen and move the first two-way switch to its other position when the second two-way switch is moved to its non-corresponding position.

12. A shield according to claim 11, wherein the first two-way switch is a sliding switch.

13. A shield according to claim 11, wherein the power source comprises a solar cell disposed on a surface of the shield exposed to a vivid light source, a battery for energizing the motor, and a diode connecting the solar cell and the battery to allow the solar cell to charge the battery.

14. A shield according to claim 13, further comprising a first transparent spatter plate for covering the opening in the body and a second transparent spatter plate for protecting the solar cell, and second and third guide means on the body for slidably accepting the first and second spatter plates, each of said second and third guide means comprising a resilient strip for urging the first or second spatter plate into engagement with the second or third guide means and allowing the second or third guide means to accept spatter plates of varying thickness.

15. A shield according to claim 5, wherein the body further comprises resilient arresting means for holding the screen when it reaches the end of its movement.

16. A shield according to claim 5, wherein the rack is in direct contact with the pinion.

* * * * *